United States Patent
Weir

(10) Patent No.: US 9,872,738 B2
(45) Date of Patent: Jan. 23, 2018

(54) METHODS, SYSTEMS, AND DEVICES FOR CONTROL OF SURGICAL TOOLS IN A ROBOTIC SURGICAL SYSTEM

(71) Applicant: Ethicon Endo-Surgery, Inc., Cincinnati, OH (US)

(72) Inventor: Michael P. Weir, Blanchester, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 91 days.

(21) Appl. No.: 14/988,839

(22) Filed: Jan. 6, 2016

(65) Prior Publication Data

US 2017/0189130 A1 Jul. 6, 2017

(51) Int. Cl.
*G06F 19/00* (2011.01)
*A61B 34/37* (2016.01)
*A61B 34/00* (2016.01)

(52) U.S. Cl.
CPC .............. *A61B 34/37* (2016.02); *A61B 34/77* (2016.02)

(58) Field of Classification Search
CPC ........ A61B 18/1442; A61B 2019/2242; A61B 2017/00867; A61B 2019/465; A61B 2019/2211; A61B 2018/00619; A61B 2018/00404; A61B 19/2203; A61B 2018/00345; A61B 34/37; A61B 34/77; C08L 2201/12
USPC ....... 700/245, 253, 257, 258, 259, 260, 261, 700/262, 264
See application file for complete search history.

(56) References Cited

U.S. PATENT DOCUMENTS

| | | | | |
|---|---|---|---|---|
| 5,876,325 A | * | 3/1999 | Mizuno | A61B 1/00048 600/102 |
| 6,587,750 B2 | * | 7/2003 | Gerbi | G06F 19/3406 128/897 |
| 8,209,054 B2 | * | 6/2012 | Howison | A61B 17/29 318/560 |
| 8,527,094 B2 | * | 9/2013 | Kumar | A61B 34/37 600/101 |
| 8,831,782 B2 | | 9/2014 | Itkowitz | |
| 9,155,592 B2 | * | 10/2015 | Itkowitz | A61B 19/2203 |
| 9,244,524 B2 | * | 1/2016 | Inoue | A61B 17/29 |

(Continued)

FOREIGN PATENT DOCUMENTS

| WO | WO-2014151621 A1 | 9/2014 |
|---|---|---|
| WO | WO-2014151952 A1 | 9/2014 |

*Primary Examiner* — Jaime Figueroa
(74) *Attorney, Agent, or Firm* — Mintz Levin Cohn Ferris Glovsky and Popeo, P.C.

(57) ABSTRACT

Various exemplary methods, systems, and devices for control of surgical tools in a robotic surgical system are provided. In general, a robotic surgical system can be configured to control a surgical instrument in one of first and second modes of operation. In the first mode, the robotic surgical system can be configured to receive an input from a master tool indicating movement of the master tool. In response to the input, the robotic surgical system can be configured to cause the instrument to corresponding move. In the second mode, the robotic surgical system can be configured to receive an input from the master tool indicating movement of the master tool, and, in response to the input, adjust a non-positional output characteristic of the instrument. The robotic surgical system can be configured to switch control of the instrument between the first and second modes.

8 Claims, 8 Drawing Sheets

(56) References Cited

U.S. PATENT DOCUMENTS

| | | | |
|---|---|---|---|
| 9,333,042 B2* | 5/2016 | Diolaiti | A61B 1/00087 |
| 9,632,577 B2* | 4/2017 | Ogawa | G06F 3/01 |
| 2003/0060927 A1* | 3/2003 | Gerbi | G06F 19/3406 |
| | | | 700/245 |
| 2009/0036902 A1* | 2/2009 | DiMaio | A61B 19/2203 |
| | | | 606/130 |
| 2009/0171371 A1* | 7/2009 | Nixon | A61B 34/30 |
| | | | 606/130 |
| 2009/0202387 A1 | 8/2009 | Dlugos, Jr. et al. | |
| 2009/0326322 A1* | 12/2009 | Diolaiti | A61B 1/00039 |
| | | | 600/112 |
| 2010/0169815 A1* | 7/2010 | Zhao | B25J 9/1633 |
| | | | 715/771 |
| 2010/0274087 A1* | 10/2010 | Diolaiti | A61B 1/00087 |
| | | | 600/118 |
| 2012/0158013 A1 | 6/2012 | Stefanchik et al. | |
| 2012/0221147 A1* | 8/2012 | Goldberg | A61B 34/30 |
| | | | 700/264 |
| 2013/0103050 A1* | 4/2013 | Richmond | A61B 34/30 |
| | | | 606/130 |
| 2013/0295540 A1* | 11/2013 | Kesavadas | G09B 23/28 |
| | | | 434/262 |
| 2014/0148820 A1* | 5/2014 | Ogawa | A61B 17/29 |
| | | | 606/130 |
| 2014/0171964 A1* | 6/2014 | Yang | A61B 34/30 |
| | | | 606/130 |
| 2015/0066051 A1* | 3/2015 | Kwon | B25J 3/04 |
| | | | 606/130 |
| 2016/0157943 A1* | 6/2016 | Mintz | B25J 9/0084 |
| | | | 606/130 |

* cited by examiner

METHODS, SYSTEMS, AND DEVICES FOR CONTROL OF SURGICAL TOOLS IN A ROBOTIC SURGICAL SYSTEM

FIELD

The present disclosure relates generally to methods, systems, and devices for control of surgical tools in a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. It can be very difficult and expensive to give true force feedback to the surgeon. Another drawback is that robotic systems traditionally only allow the surgeon to control movement of up to two surgical instruments, with any other surgical instruments having to be manually controlled by other medical personnel. It can be difficult for the surgeon and other medical personnel to communicate and synchronize activities of the separately controlled instruments during performance of a surgical procedure.

Accordingly, there remains a need for improved methods, systems, and devices for control of surgical tools in a robotic surgical system.

SUMMARY

In one embodiment, a surgical system is provided that includes first and second slave tools each having a working end configured to be positioned within a patient during performance of a surgical procedure, a master tool configured to be manually manipulated by a user to control the first and second slave tools, and a controller configured to be in electronic communication with the first and second slave tools and with the master tool. The controller can be configured to receive a first input from the master tool indicating movement of the master tool and to cause the first slave tool to move in position in response to the received first input, and the controller can be configured to receive a second input from the master tool indicating movement of the master tool and to adjust a force output of the second slave tool in response to the received second input.

The system can vary in any number of ways. For example, the controller can be configured to receive a third input from the master tool and, in response to receiving the third input, to cause subsequently received first inputs to control the second slave tool instead of the first slave tool and to cause subsequently received second inputs to control the first slave tool instead of the second slave tool. For another example, the first input can indicate a change in position of the master tool, and the controller can be configured to cause the slave tool to move in position by either mimicking or mirroring the master tool's change in position indicated by the first input. The second input can indicate a change in position of the master tool, and the controller can be configured to translate an amount of the master tool's change in position indicated by the second input to an amount of the adjusted force output. For still another example, the second input can indicate a translational movement or a rotational movement of the master tool. When the second input indicates the translational movement, adjusting the force output of the second slave tool in response to the received second input can include causing the second slave tool to rotate, and when the second input indicates the rotational movement, adjusting the force output of the second slave tool in response to the received second input can include causing the second slave tool to translate. For yet another example, the first and second tools can each be configured to move in multiple degrees of freedom. The first input can indicate movement of the master tool in at least two of the multiple degrees of freedom, and the controller can be configured to cause the first slave tool to move in the at least two of the multiple degrees of freedom in response to the received first input. The second input can indicate movement of the master tool in one of the multiple degrees of freedom, and the controller can be configured to correlate the movement in the one degree of freedom to the force output. For still another example, the system can include a motor. The first input can cause the controller to adjust a torque provided by the motor to the first slave tool, and the second input can cause the controller to adjust a torque provided by the motor to the second slave tool.

In another embodiment, a surgical system is provided that includes a first slave tool and a master tool. The first slave tool can be configured to apply a force to a target during performance of a surgical procedure, and the first slave tool can be configured to move in a maximum number of degrees of freedom. The maximum number can be a plural number. The master tool can be configured to control the first slave tool in a first mode in which movement of the master tool in one or more of the degrees of freedom causes the first slave tool to correspondingly move in the one or more of the degrees of freedom, and the master tool can be configured to control the first slave tool in a second mode in which movement of the master tool in one of the degrees of freedom causes an amount of the applied force to change based on an amount of the movement in the one degree of freedom.

The system can have any number of variations. For example, in response to a user input to the surgical system, the master tool can be configured to switch between controlling the first slave tool in the first mode and controlling the first slave tool in the second mode. For another example, the system can include a second slave tool configured to move in the maximum number of degrees of freedom. The master tool can be configured to control the first slave tool in the first mode and the second slave tool in the second mode. In response to a user input to the surgical system, the master tool can be configured to switch from controlling the first slave tool in the first mode and the second slave tool in the second mode to controlling the second slave tool in the first mode and the first slave tool in the second mode. For yet another example, the system can include a plurality of additional slave tools. Only one of the first slave tool and the plurality of additional slave tools can be controlled by the master tool in the first mode, with a remainder of the first slave tool and the plurality of additional slave tools being controlled by the master tool in the second mode. The master tool can be configured to, in response to a user input to the surgical system, change which one of the first slave tool and the plurality of additional slave tools is controlled by the master tool in the first mode. For still another example, changing the amount of the applied force can be configured to not correspondingly move the first slave tool in one degree of freedom. For another example, the system can include a controller configured to be in electronic communication with the first slave tool and the master tool. The controller can be configured to control the movement of the first slave tool in response to the input to the master tool in the first mode and to control the changed applied force in response to the input to the master tool in the second mode. The system can include a motor configured to provide a force to the first slave tool, and the controller can adjust the amount of force provided by the motor to the first slave tool in response to the input to the master tool in the second mode. For yet another example, the maximum plural number of degrees of freedom can include at least one translational degree of freedom and at least one rotational degree of freedom.

In another aspect, a surgical method is provided that in one embodiment includes positioning a working end of a first slave tool relative to a first target relevant to performance of a surgical procedure on a patient, positioning a working end of a second slave tool relative to a second target relevant to performance of the surgical procedure such that the second slave tool applies a force to the second target, and moving a master tool electrically coupled to the first and second slave tools. The movement of the master tool when the master tool is in a first mode of operation can cause corresponding movement of the first slave tool relative to the first target, and the movement of the master tool when the master tool is in a second mode of operation can cause an amount of the force applied to the second target to be changed by an amount corresponding to a scale of the movement of the master tool.

The method can vary in any number of ways. For example, the method can include swapping modes of the master tool such that the movement of the master tool when the master tool is in the first mode of operation causes corresponding movement of the second slave tool relative to the second target, and the movement of the master tool when the master tool is in the second mode of operation causes an amount of a force applied to the first target by the first slave tool to be changed by an amount corresponding to the scale of the movement of the master tool.

For another example, the movement of the master tool can be in multiple degrees of freedom. The movement of the master tool when the master tool is in the first mode of operation can cause the first slave tool to move in the multiple degrees of freedom relative to the first target, and the movement of the master tool when the master tool is in the second mode of operation can not cause the second slave tool to move in the multiple degrees of freedom relative to the second target. For yet another example, the movement of the master tool when the master tool is in the second mode of operation can include movement of the master tool translationally or rotationally, and causing the amount of the force applied to the second target to be changed can include causing the second slave tool to move in the other one of translationally and rotationally.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This invention will be more fully understood from the following detailed description taken in conjunction with the accompanying drawings, in which.

DETAILED DESCRIPTION

Figure 1:
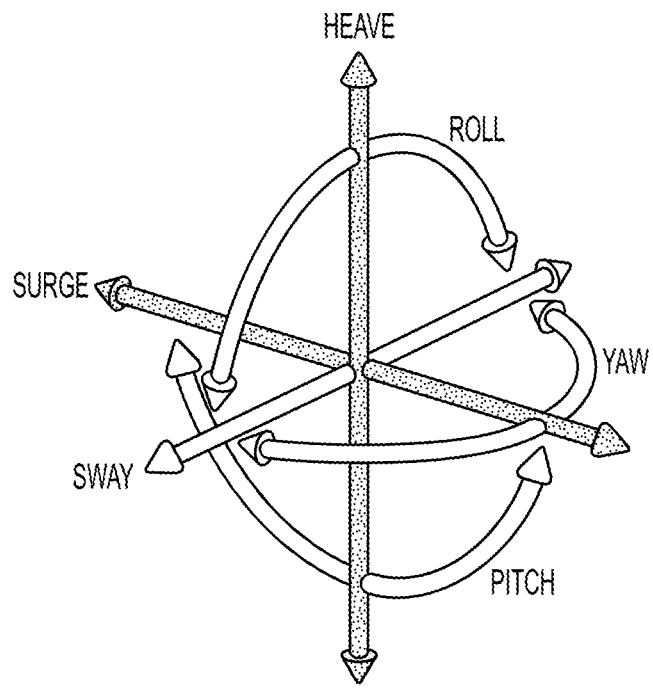
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for control of surgical tools in a robotic surgical system are provided. In general, a robotic surgical system can be configured to control a surgical instrument in one of first and second modes of operation. In the first mode of operation, the robotic surgical system can be configured to receive an input from a master tool indicating movement of the master tool, such as manual movement thereof by a user (e.g., a surgeon, a surgical assistant, a medical student, etc.). In response to the input, the robotic surgical system can be configured to cause a surgical instrument coupled to the robotic surgical instrument to correspondingly move. The robotic surgical system can thus, in the first mode of operation, be configured to translate a change in position of the master tool to a change in position of the surgical instrument. In other words, in the first mode of operation, the robotic surgical system can be configured to translate a pose of the master tool to another pose for the surgical instrument's change in position. As will be appreciated by a person skilled in the art, a pose can be defined by a plurality of elements or variables, such as three elements representing translational movement (e.g., surge, heave, and sway) and three elements representing rotational movement (e.g., roll, pitch, and yaw). In the second mode of operation, the robotic surgical system can be configured to receive an input from the master tool indicating movement of the master tool by the user, and, in response to the input, adjust a non-positional output characteristic of the surgical instrument. The robotic surgical system can thus, in the second mode of operation, be configured to translate a pose of the master tool to an output characteristic of the surgical instrument, e.g., to a non-pose output. In an exemplary embodiment, the output characteristic of the surgical instrument can include a force output of the surgical instrument such as a force being applied to a target (e.g., a tissue, a surgical accessory such as a suture or gauze, another surgical instrument, etc.) by the surgical instrument, a speed of the surgical instrument relative to a target, a displacement of the surgical instrument relative to a target, and an acceleration of the surgical instrument relative to a target. The robotic surgical system can be configured to switch control of the surgical instrument between the first and second modes of operation, thereby providing flexibility in control of the instrument.

By being operable in the first and second modes, the robotic surgical system can allow a master tool to control a surgical instrument in two different ways, one that changes the instrument's position and another that does not. Thus, the user can have more control of the surgical instrument during performance of a surgical procedure, and/or the user can more finely control the surgical instrument (e.g., through the output adjustment in the second mode of operation). The robotic surgical system being operable in the first and second modes of operation can save time during the surgical procedure since the user need not switch between master tools to control the surgical instrument in different ways and/or can facilitate easy use of the robotic surgical system since the user need only learn use of the master tool instead of two different tools to manipulate the surgical instrument in two different ways.

The robotic surgical system can be configured to control a plurality of surgical instruments (e.g., two, three, four, etc.) with one of the surgical instruments being controlled in the first mode and a remainder of the surgical instruments being controlled in the second mode. The robotic surgical system can be configured to switch control of the various surgical instruments between the first and second modes, thereby allowing the user to choose which of the instruments is controlled in the first mode to change in position and which of the instruments are configured to be controlled in the second mode to have their output changed. The robotic surgical system can thus be configured to allow a user to control one of the surgical instruments as a primary instrument that is actively manipulating tissue and/or other matter at a surgical site (e.g., cutting the tissue, cauterizing the tissue, retracting the tissue, etc.), and to control the remainder of the surgical instruments as secondary instruments that are being held in a substantially fixed position at the surgical site. A person skilled in the art will appreciate that a surgical instrument may not be held in a precisely fixed position during a surgical procedure for any of a variety of reasons (e.g., the patient's breathing causing instrument movement, the patient's blood flow causing instrument movement, etc.) but nevertheless be considered to be in a substantially fixed position. One example of a secondary instrument includes a grasper grasping tissue at a surgical site and holding the tissue in a substantially fixed position, such as with retraction. During the course of a surgical procedure, a user may determine that the grasper needs to tension the tissue more by pulling the tissue harder, e.g., because of movement of adjacent tissue, because of introduction of a surgical accessory into the surgical space, etc., and accordingly adjust an output of the secondary instrument to cause the greater tensioning (e.g., alter displacement of the grasper). Another example of a secondary instrument includes a guidewire translating through a vascular lumen that a user may desire to move slower through the lumen and accordingly adjust a scalar output of the secondary instrument to cause the guidewire's velocity to decrease. Yet another example of a secondary instrument includes a grasper holding a suture tied in a knot. During the course of a surgical procedure, a user may determine that the knot needs to be tighter and accordingly adjust a scalar output of the secondary instrument to cause the suture to be pulled so as to tighten the knot (e.g., alter displacement of the grasper).

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
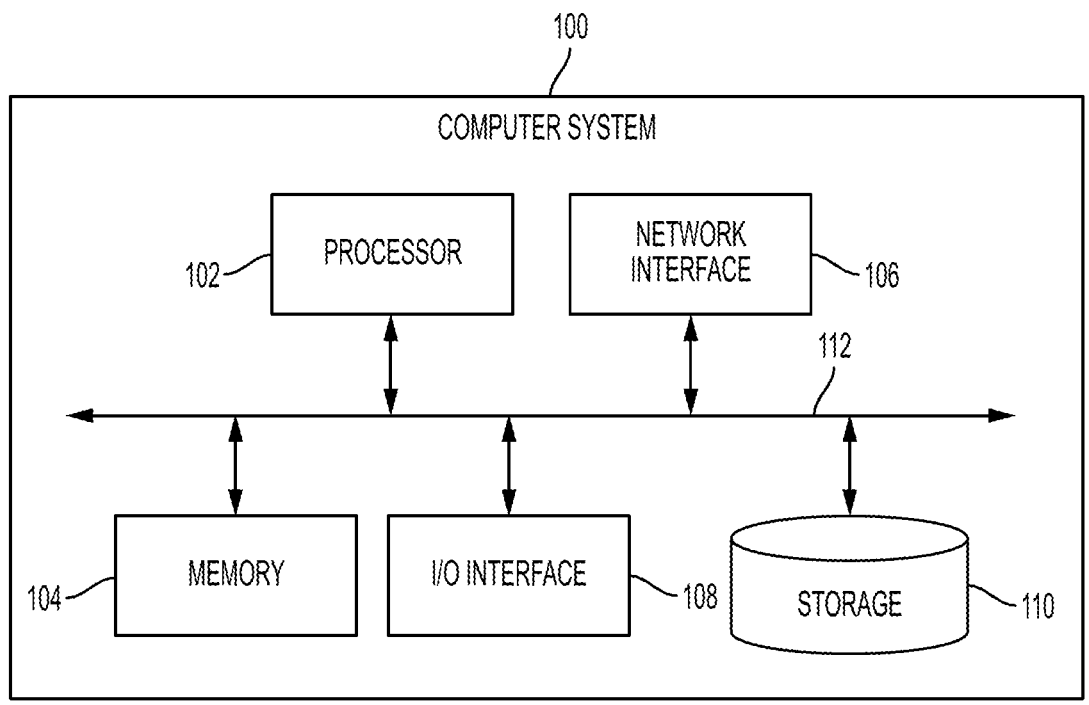
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
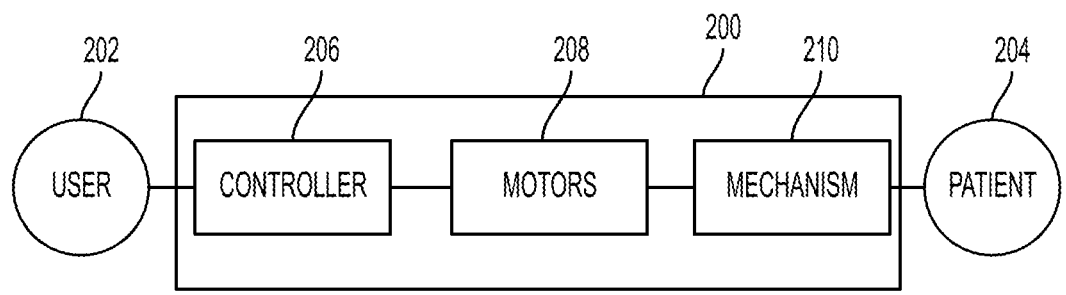
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
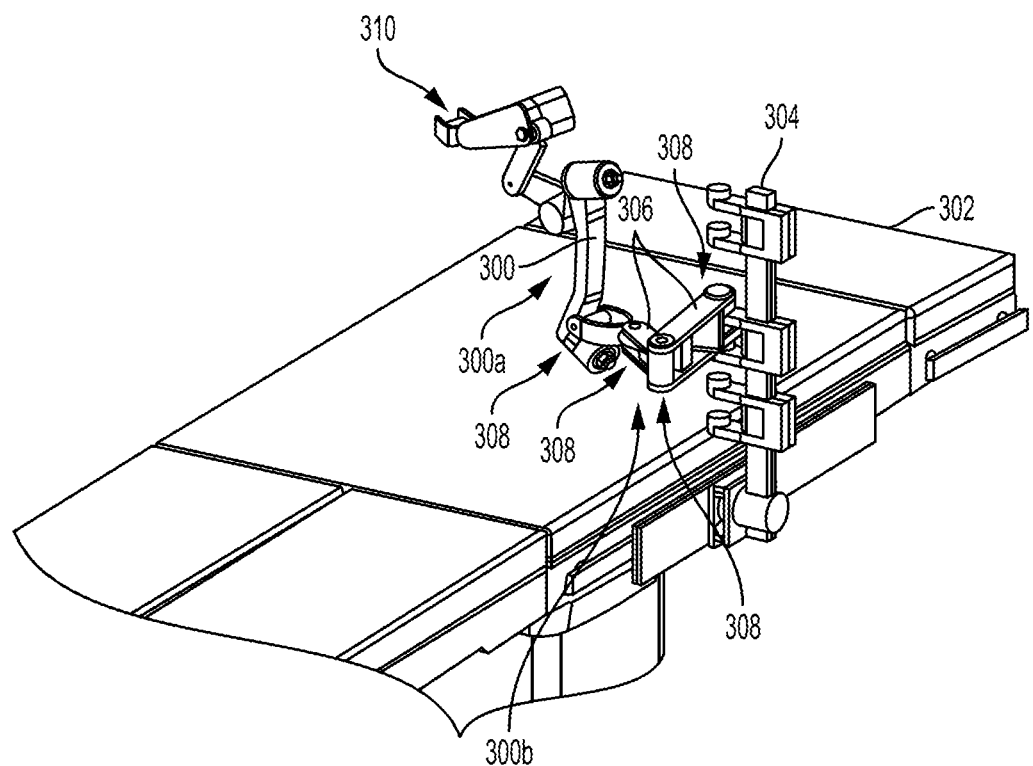
FIG. 4 is a perspective view of one embodiment of an arm of a robotic surgical system, the arm being mounted to a surgical table.
Figure 5:
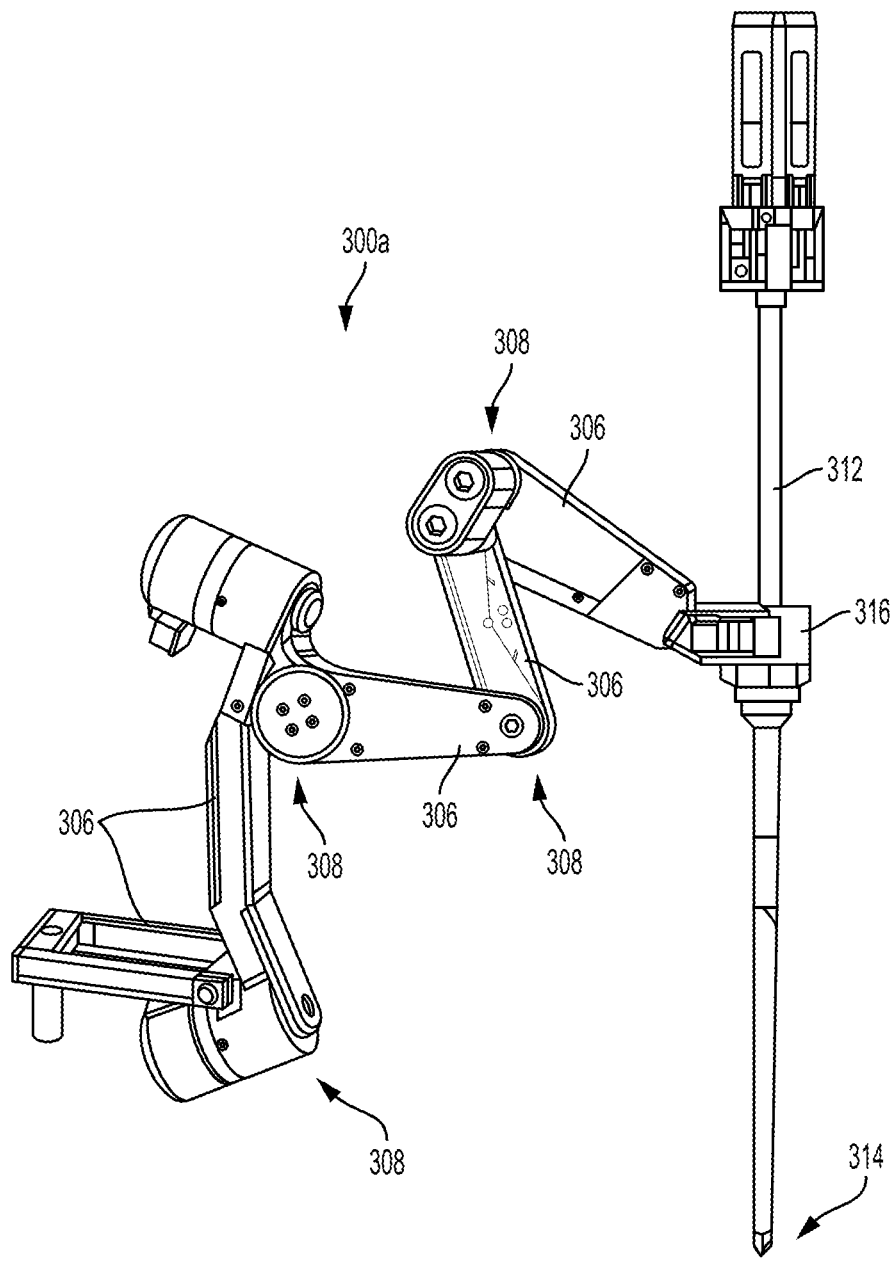
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
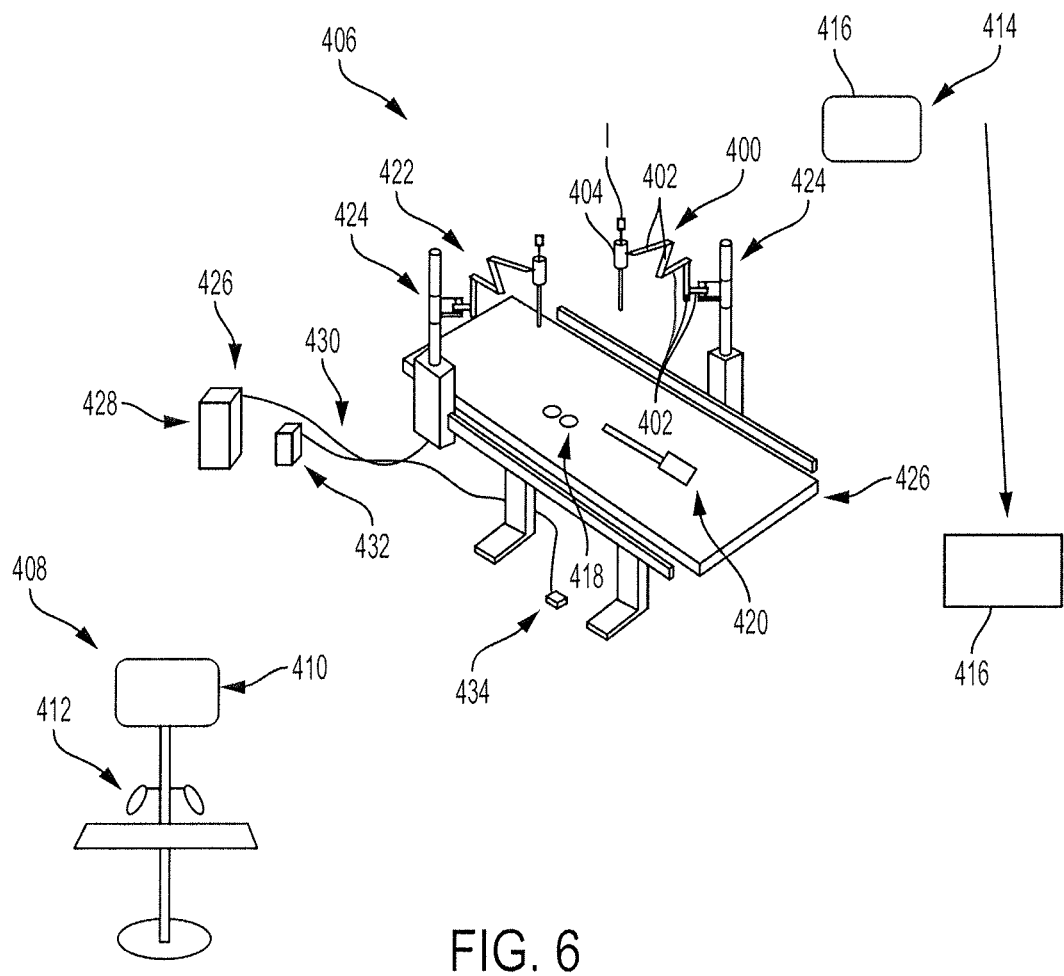
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the arms 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
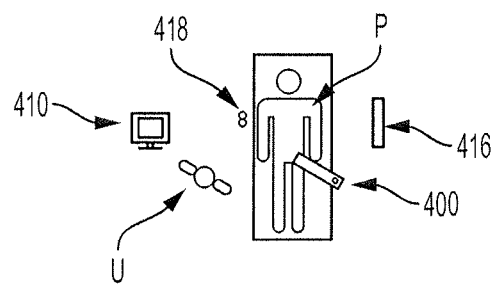
FIG. 7 is a schematic view of one embodiment of the robotic surgical system of FIG. 6 in use during performance of a surgical procedure on a patient.
Figure 8:
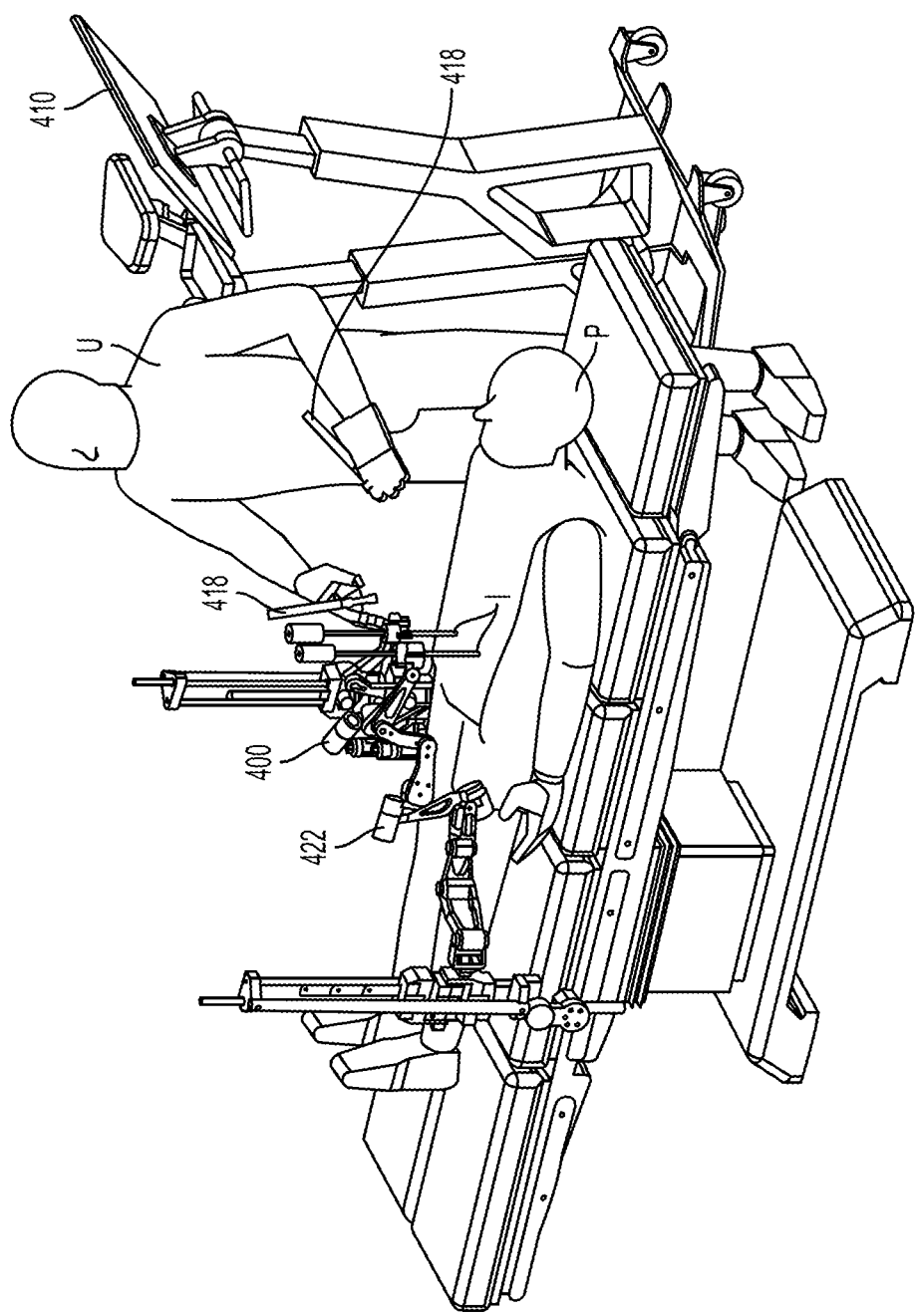
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arms 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device. The robotic surgical system 406 can include at least one knee control (not shown) coupled to the computer 428 via one of the cables 430, similar to a knee control of a sewing machine, which can allow the knee control to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
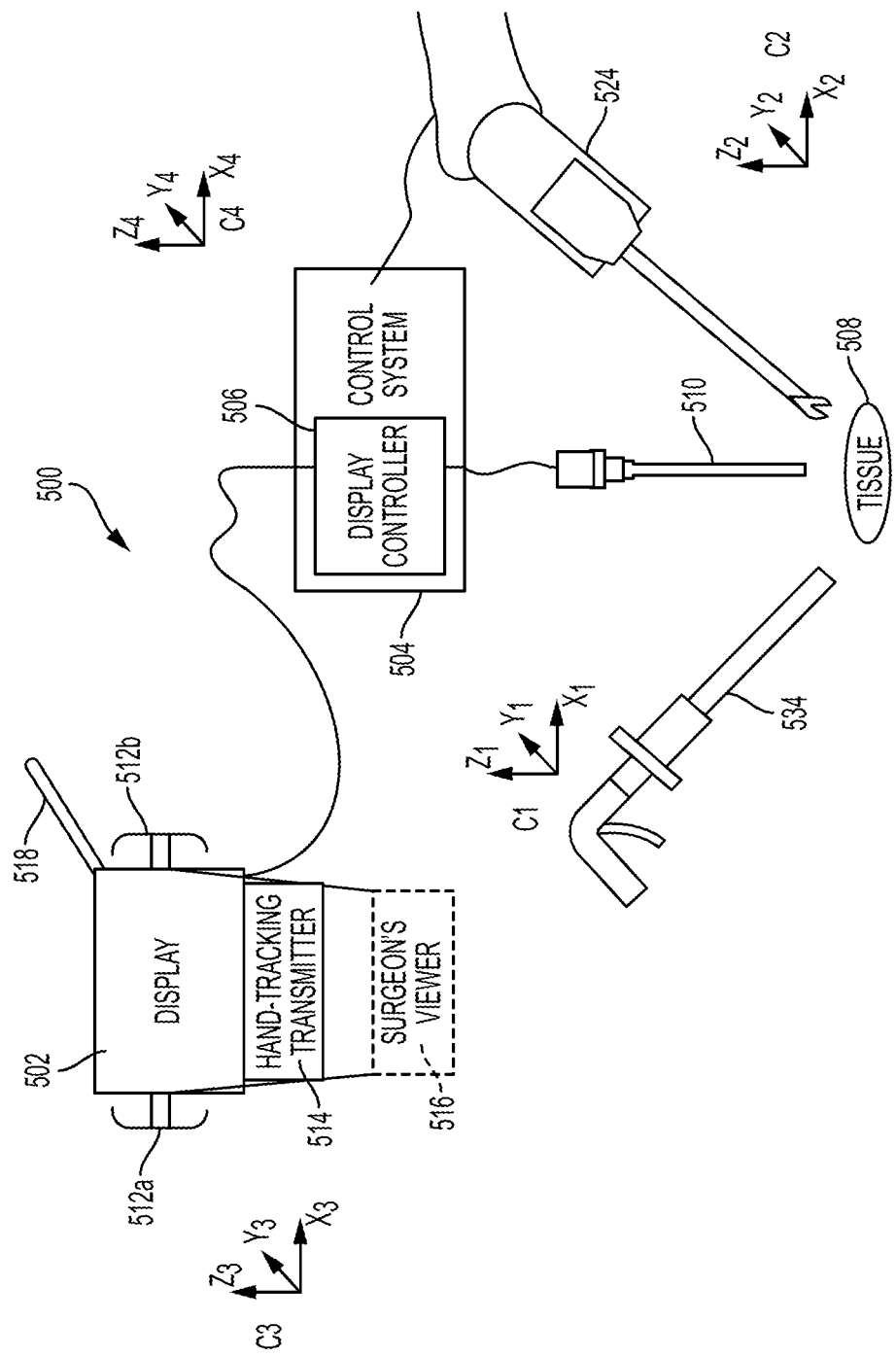
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
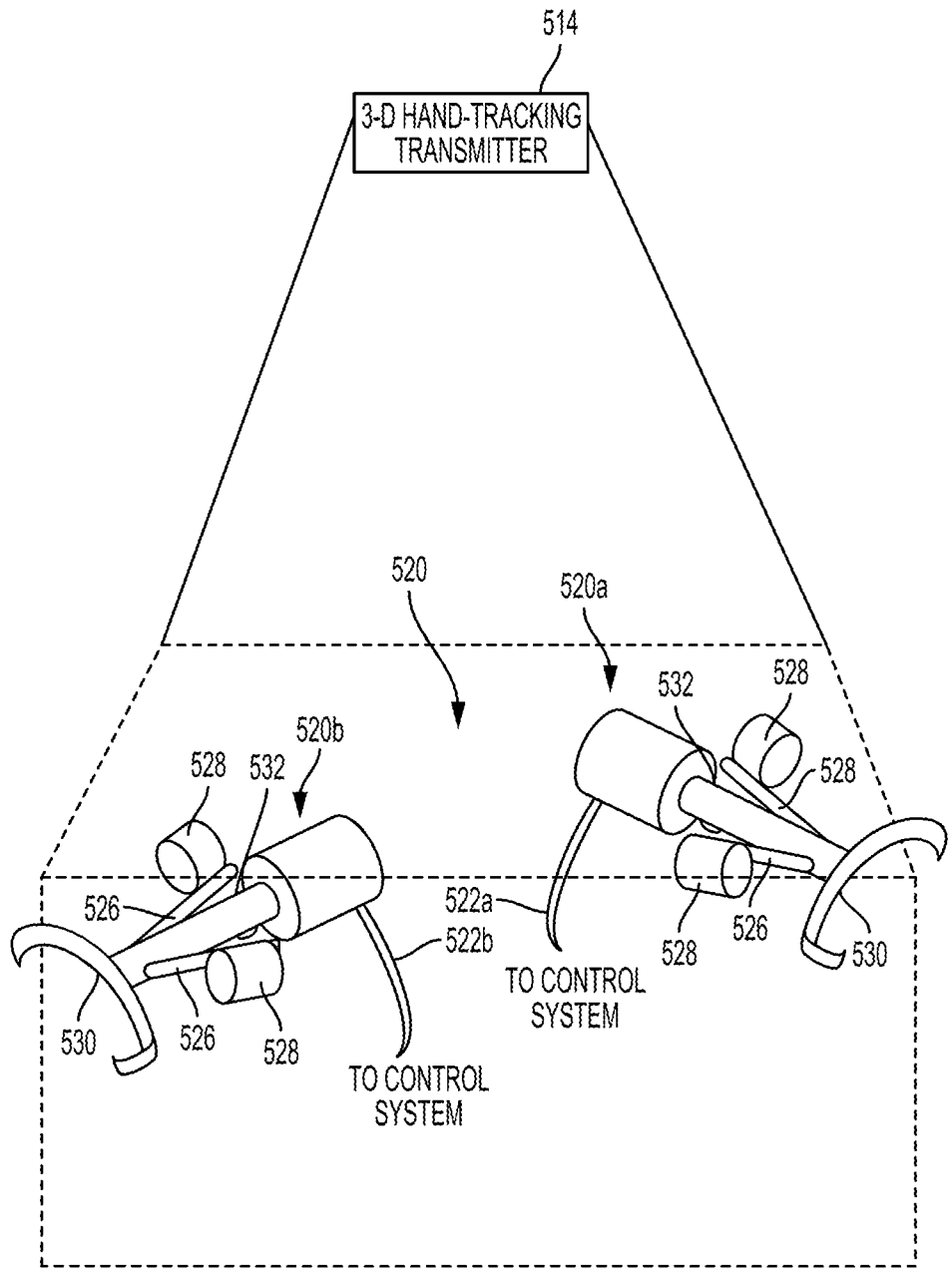
FIG. 10 is a perspective view of one embodiment of a master tool in a field generated by a transmitter of the robotic surgical system of FIG. 9.

Movement of a user-controlled master tool 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522a, 522b. The control system 504, e.g., a processor thereof, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. The control system 506 can be configured to always orient the display 502 so that the first, second, and third coordinate systems C1, C2, C3 are aligned to the third coordinate system C3. For example, if the user is holding the master tool 520, e.g., one of the first and second master tool grips 520a, 520b, in one of his/her hands and moves that hand to his/her right, thereby moving the held master tool 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Figure 11:
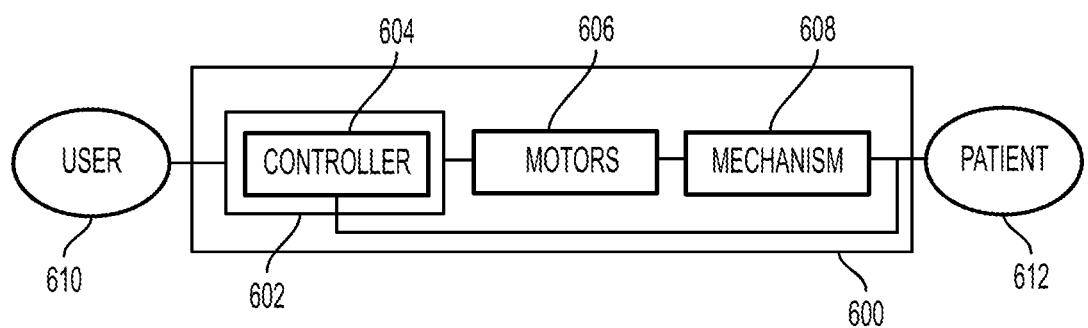
FIG. 11 is a schematic view of another embodiment of a robotic surgical system configured to be operated by a user and to be used during performance of a surgical procedure on a patient.

As mentioned above, a robotic surgical system can be configured to control a surgical instrument (e.g., an instrument removably and replaceably coupled to an arm of the robotic surgical system) in one of first and second modes of operation. FIG. 11 illustrates one embodiment of such a robotic surgical system 600. The robotic surgical system 600 can generally be configured and used similar to the robotic surgical system 200 of FIG. 3. The robotic surgical system 600 can include a computer system 602 that includes a controller 604, motors 606, and a movement mechanism 608 (e.g., an electromechanical arm). The controller 604 can be configured to receive an input from a user 610 requesting movement, relative to the patient 612, of a surgical instrument (not shown) coupled to the movement mechanism 608. The user can provide the input using a master tool (not shown) in electronic communication with the computer system 602, as described herein. The controller 604 can be configured to cause the motors 606 to drive movement of the movement mechanism 608, thereby causing the movement of the surgical instrument requested by the user 610.

The robotic surgical system 600 can be configured to switch between the first and second modes of operation in a variety of ways. For example, the master tool can include a mode control mechanism (e.g., a mode control button similar to the mode control button 532 of the master tool 520 embodiment of FIG. 10, a mode control lever on the master tool, etc.) configured to be actuated by the user 610 to switch between the first and second modes. For another example, the computer system 602 can include an IO device configured to allow the user 610 to switch between the first and second modes, e.g., by user 610 input to an IO interface in the form of a keyboard, pointing device, etc. For yet another example, the master tool can include a plurality of different controls with at least one of the controls dedicated to the first mode and at least one other of the controls dedicated to the second mode. At least one of the controls can be dedicated to the first mode of operation and be configured to cause an input for the first mode of operation to be transmitted to the robotic surgical system 600. At least one other of the controls can be dedicated to the second mode of operation and be configured to cause an input for the second mode of operation to be transmitted to the robotic surgical system 600. The other one(s) of the controls dedicated to the second mode can be calibrated to accept input thereto in a predetermined direction of a coordinate system associated with the user 610 (e.g., moving the other control(s) along the x axis by extending the ring and little fingers, etc.) and/or about a predetermined axis of the coordinate system (e.g., rotating the other control(s) about the x axis by rotating the ring and little fingers clockwise, rotating the other control(s) about the x axis by rotating the ring and little fingers closer to the user's viewpoint, etc.). This calibration can help prevent manipulation of the control(s) dedicated to the first mode from inadvertently causing an input to the dedicated second mode control(s) and/or can help compensate for a reduced dexterity of digit(s) holding and manipulating the dedicated second mode control(s), such as in the case of ring fingers and little fingers that typically have less dexterity than other fingers and the thumb. One example of a master tool including a plurality of different controls includes a handheld master tool having a first portion thereof dedicated to the first mode and configured to be held and manipulated by a user's thumb, index finger, and middle finger, and having a second portion thereof dedicated to the second mode configured to be held and manipulated by a user's ring finger and little finger. Another example of a master tool including a plurality of different controls includes a handheld master tool dedicated to the first mode and a foot pedal master tool dedicated to the second mode. Another example of a master tool including a plurality of different controls includes a handheld master tool dedicated to the first mode and a knee control master tool dedicated to the second mode.

In an embodiment in which the robotic surgical system 600 is controlling only one surgical instrument, e.g., when only one surgical instrument is coupled to the movement mechanism 608, switching between the first and second modes can cause the robotic surgical system 600 to switch between controlling the surgical instrument in the first and second modes.

In an embodiment in which the robotic surgical system 600 is controlling two surgical instruments, e.g., when first and second surgical instruments are coupled to the movement mechanism 608, which as mentioned herein can include one or more movement mechanisms 608, the computer system 602 can be configured to allow user designation of one of the first and second surgical instruments as a primary one of the instruments to be controlled in the first mode of operation and to allow user designation of the other of the first and second the surgical instruments as a secondary one of the instruments to be controlled in the second mode of operation. For example, the computer system 602 can include an IO interface (a keyboard, pointing device, etc.) (not shown) configured to facilitate user selection of the primary and secondary instruments using the computer system 602. Switching between the first and second modes can cause the robotic surgical system to switch between controlling the primary surgical instrument in the first mode (e.g., movement of the master tool controls the primary surgical instrument) and controlling the secondary surgical instrument in the second mode (e.g., movement of the master tool controls the secondary surgical instrument).

In an embodiment in which the robotic surgical system 600 is controlling three or more surgical instruments, e.g., when three or more surgical instruments are coupled to the movement mechanism 608, the computer system 602 can be configured to allow user designation of one of the surgical instruments as a primary one of the instruments to be controlled in the first mode of operation and to allow user designation of a remainder of the surgical instruments as secondary one(s) of the instruments to be controlled in the second mode of operation, such as by user 610 input to an IO interface of the computer system 602. Switching between the first and second modes can cause the robotic surgical system to switch between controlling the primary surgical instrument in the first mode (e.g., movement of the master tool controls the primary surgical instrument) and controlling one of the secondary surgical instruments in the second mode (e.g., movement of the master tool controls the one of the secondary surgical instruments). The one of the secondary surgical instruments being controlled in the second mode can be selected by the user 610 in a variety of ways, such as by a secondary instrument selection mechanism of the master tool, e.g., a button, lever, etc., or by input to an IO interface of the computer system 602.

Figure 12:
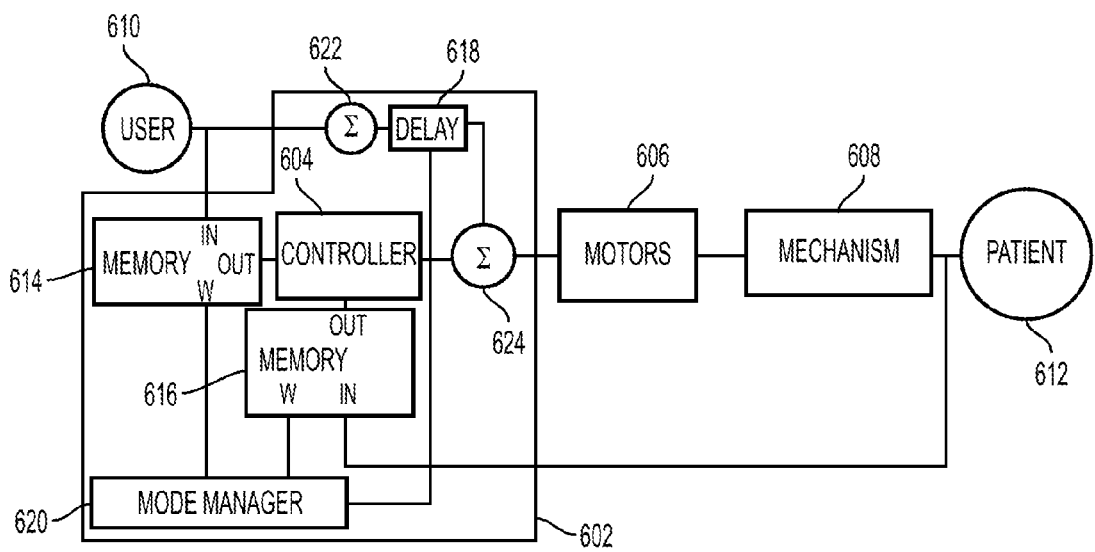
FIG. 12 is another schematic view of the robotic surgical system of FIG. 11.

As shown in FIG. 12, the computer system 602 can include, in addition to the controller 604, a first memory 614 configured to be in communication with the controller 604; a second memory 616 configured to be in communication with the controller 604; a delay element 618 (e.g., a memory); a mode manager 620 configured to be in communication with the first memory 614, the second memory 616, and the delay element 618; a first summer 622 configured to be in communication with the delay element 618; and a second summer 624 configured to be in communication with the delay element 618. As illustrated in FIG. 12, the first memory 614 can be configured to receive position input from the master tool and store the position input therein, and the second memory 616 can be configured to receive feedback input from the movement mechanism 608 and store the feedback input therein. The first and second memories 614, 616, the delay element 618, the mode manager 620, the first summer 622, and the second summer 624 can be configured to facilitate operation of the robotic surgical system 600 in the first and second modes of operation, as discussed further below.

In the first mode of operation, the controller 604 can be configured to receive a first signal from the master tool indicative of the master tool's movement by the user 610 and, in response to receipt of the first signal, cause the primary surgical instrument (or in the case of a single instrument being coupled to the movement mechanism 608, that one instrument) to correspondingly move as described herein for the first mode of operation. The first signal can indicate a pose of the master tool relative to a first coordinate system, e.g., a coordinate system associated with the user 610 and the master tool. In response to the first signal, the controller 604 can be configured to cause corresponding movement of the surgical instrument in a second coordinate system, e.g., a coordinate system associated with the surgical instrument. The corresponding movement of the surgical instrument can mirror the movement of the master tool (e.g., move in a direction opposite to a direction in which the master tool moved), can mimic the movement of the master tool (e.g., move in a same direction in which the master tool moved), or can move in a direction indicated by the master tool (e.g., move in a direction in which the master tool in the form of a joystick is moved, move in a direction indicated by touch on the master tool in the form of a touch screen, move in a direction indicated by rolling of the master tool in the form of a roller ball, etc.).

For example, the first signal can include a first vector value (e.g., magnitude and direction) indicating direction and magnitude of the master tool's movement relative to the first coordinate system. The controller 604 can be configured to translate the first vector value to a second vector value representing the desired movement of the surgical instrument in the second coordinate system. The translation of the first vector value to the second vector value can vary based on how movement of the master tool is configured to correspond to movement of the surgical instrument. The second vector value can be reflective of mirrored movement, mimicked movement, or directional movement. As will be appreciated by a person skilled in the art, the first and second vector values can be represented by a polynomial that can include a complex variable.

The controller 604 can be configured transmit a second signal to the motors 606 indicative of the second vector value. The second signal can cause the motors 606 to generate a torque in response to receipt of the second signal. The torque can cause movement of the movement mechanism 608, e.g., acceleration of the movement mechanism 608 in proportion to the torque, thereby moving the surgical instrument coupled thereto. In at least some embodiments, the second signal from the controller 604 can cause the motors 606 to exert a maximum possible torque to bring the position of the surgical instrument into accordance with the position of the master tool. Then, once the intended position of the surgical instrument has been reached, the torque provided by the motors 606 can be reduced to a degree effective to maintain the surgical instrument in the intended position. The maximum possible torque of the motors 606 may not be, as will be appreciated by a person skilled in the art, an absolute maximum possible torque of the motors 606 but instead be a maximum permissible torque of the motors 606 that is less than the absolute maximum possible torque of the motors 606 in order to, e.g., improve safety, reduce chances of motor burnout, etc.

In the second mode of operation, the controller 604 can be configured to receive a third signal from the master tool indicative of the master tool's movement by the user 610 and, in response to receipt of the third signal, cause the secondary surgical instrument (or in the case of one surgical instrument being coupled to the movement mechanism 608, that one instrument) to correspondingly adjust its output as described herein for the second mode of operation. Depending on the configuration of the master tool and/or on the force output being adjusted, the adjustment in the output can be achieved by a direction of the output being adjusted in a same direction or in a different direction as the master tool's movement. For an example of the case of the same direction, movement of the master tool along an x-axis of a coordinate system associated with the master tool causing a force output of the secondary surgical instrument to change along an x-axis of a coordinate system associated with the secondary surgical instrument. For an example of the case of the different direction, rotational movement of the master tool about an x-axis of a coordinate system associated with the master tool causing a force output of the secondary surgical instrument to change by translating the secondary surgical instrument along an x-axis of a coordinate system associated with the secondary surgical instrument. In general, when the secondary surgical instrument's direction is different than the master tool's direction, the directions can be opposite ones of rotation and translation such that translation of the master tool can cause rotation of the second surgical instrument, and rotation of the master tool can cause translation of the second surgical instrument.

For example, similar to the first signal and the first vector value discussed above with respect to the first mode of operation, the third signal can include a third vector value indicating direction and magnitude of the master tool's movement relative to a coordinate system. The controller 604 can be configured to translate the third vector value to a scalar value (e.g., magnitude only) representing the desired output adjustment of the surgical instrument. The scalar value can be in proportion to the third vector value, or it can have a differential or integral relationship to the third vector value. The third vector can be relative to one coordinate system, e.g., a coordinate system associated with the user 610 and the master tool, and the scalar value can be relative to another coordinate system, e.g., a coordinate system associated with the secondary surgical instrument. The controller 604 can be configured transmit a fourth signal to the motors 606 indicative of the scalar value. Similar to the second signal discussed above with respect to the first mode of operation, the fourth signal can cause the motors 606 to generate a torque in response to receipt of the fourth signal. The torque can cause movement of the movement mechanism 608, e.g., acceleration of the movement mechanism 608 in proportion to the torque, thereby changing the output of the surgical instrument coupled thereto. The controller 604 can thus be configured to cause the movement mechanism 608 to move in more degrees of freedom than the degrees of freedom indicated by the master tool, e.g., a plurality of degrees of freedom versus one degree of freedom. In at least some embodiments, similar to that discussed above regarding the second signal in the first mode of operation, the fourth signal from the controller 604 can cause the motors 606 to exert a maximum possible torque to achieve the desired output of the surgical instrument as indicated by the movement of the master tool and then reduce the torque exertion of the motors 606 to a degree effective to maintain the output of the surgical instrument.

The computer system 602 can be configured to facilitate the controller's processing of the second signal in the first mode to cause the surgical instrument's positional change and the controller's processing of the fourth signal in the second mode to cause the surgical instrument's non-positional change. The delay element 618 can store an initial default value, e.g., zero. In the first mode of operation, the mode manager 620 can be configured to issue write commands to the first and second memories 614, 616 rapidly so that there is substantially no delay between the receipt of a signal (e.g., position input from the master tool) at the input of the first memory 614 and output from the output of the first memory 614 to the controller 604, and so that there is substantially no delay between the receipt of a signal (e.g., feedback input from the movement mechanism 608) at the input of the second memory 616 and output from the output of the second memory 616 to the controller 604. A person skilled in the art will appreciate that a delay may not be precisely zero but nevertheless be considered to be substantially no delay due to one or more factors such as, e.g., very small delays inherent in electronic communication using electronic components. In the first mode of operation, the delay element 618 can remain at its default value.

In the second mode of operation, the mode manager 620 can be configured to not issue write commands to the first memory 614 in response to position input from the master tool, and to not issue write commands to the second memory 616 in response to feedback input from the movement mechanism 608. The output of the controller 604 can thus be configured to remain constant in the second mode of operation since the first and second memories 614, 616 are not receiving new data that would result in output to the controller 604. The output of the controller 604 can thus be configured to remain constant such that the surgical instrument's position can remain constant. In the second mode of operation, the mode manager 620 can be configured to output to the delay element 618 so as to update the delay element 618, e.g., change the default value of the delay element 618. As long as the user 610 does not provide input to the computer system 602, e.g., does not provide input to the master tool, the output of the delay element 618 and the input to the motors 606 can remain the same. When the user 610 provides an input to the computer system 602, the output of the delay element 618 and the input to the motors 606 can each change. The input to the computer system 602 can be transmitted through the first summer 622 to the delay element 618. One delay cycle later (e.g., a small fraction of a second), the input received at the delay element 618 can be output from the delay element 618 to the motors 606 via the second summer 624. This input to the motors 606 can serve as a torque command to the motors 606. The motors 606 can thereby cause movement of the movement mechanism 608 and hence of the surgical instrument coupled thereto where the movement manifests as an additional force so as to adjust the output of the surgical instrument. The first summer 622 can be configured to add the previous increment received thereby to the present input from the user 610, such as by the first summer 622 including an accumulator or a digital equivalent of an integrator. Thus, as long as the user 610 provides a non-zero input to the computer system 602, e.g., provides input to the master tool, the output of the first summer 622 can ramp up or down, depending on the polarity (positive or negative) of the user's input. Accordingly, in the second mode of operation, the user 610 can briefly apply an input to the master tool and promptly remove the input.

The computer system 602, e.g., the first summer 622 thereof, can be configured to cause a sustained increment to be transmitted to the motors 606, thereby resulting in a sustained increment of applied force to the movement mechanism 608, and hence to the surgical instrument coupled thereto. The incremental force can be stopped by the user 610 in multiple ways. For example, the user 610 can briefly apply a second input to the master tool in an opposite direction to the input that began the incremental force and thereby remove the second input, thereby normalizing the increment to zero. For another example, the user 610 can switch from the second mode to the first mode, thereby causing the mode manager 620 to change output of the delay element 618 to its default value, e.g., reduce the delay element's output to zero, and allow writing to the first and second memories 614, 616.

The computer system 602 can optionally be configured to adjust for a change in the surgical instrument's position in response to adjustment of the instrument's output in the second mode of operation, as such a change in position may have been inadvertent to achieve the desired output change and hence been unintended by the user 610. In other words, if the instrument ends up in a new position after application of the interim force commands in the second mode of operation, e.g., due to altering a direction of the instrument, due to altering a displacement of the surgical instrument, etc., the computer system 602 can be configured to correct for this change. The computer system 602 can be configured to provide a transient as the position of the surgical instrument is again slaved to input from the user 610, e.g., the position of the instrument is matched to input from the user 610. The mode manager 620 can be configured to write feedback input from the movement mechanism 608 to both of the first and second memories 614, 616, before closing the feedback loop. In this way, it can appear to the controller 604 that no positional change of the instrument occurred since the position would match in the first and second memories 614, 616, thereby preventing the controller 604 from attempting to cause a change in the position of the surgical instrument to the instrument's position indicated in the first memory 614 per the previous input in the first mode of operation, e.g., to the position prior to the output adjust in the second mode of operation.

Figure 13:
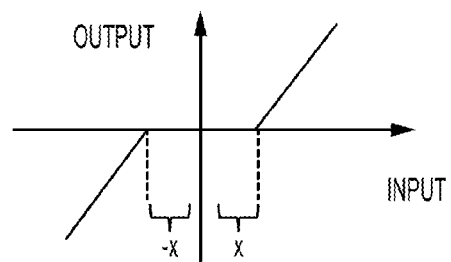
FIG. 13 is a graph showing one embodiment of force input versus force output including a deadband in a transfer function.

The computer system 602 can optionally be configured to ignore input from the user 610, e.g., to ignore input from the master tool, that represents an amount of master tool movement below a predetermined minimum amount of movement. This can help prevent inadvertent user 610 movements of the master tool from causing movement of the surgical instrument coupled to the movement mechanism 608 and/or can help prevent inadvertent jostling of the master tool from causing movement of the surgical instrument coupled to the movement mechanism 608. FIG. 13 illustrates an embodiment of this functionality with "X" representing the predetermined minimum amount. The value of X can vary based on any of a variety of factors, such as the type of master tool, the sensitivity of the master tool, the type of movement mechanism 608, etc. The positive value of X represents input in one direction and the negative value of X represents input in a direction opposite thereto. In this way, the combination of −X and X (i.e., the value of 2X) can be configured as a deadband in which input from the user 610, e.g., from the master tool, is ignored. The computer system 602 can include a deadband element (not shown) between the input from the user 610 and the first summer 622 that can be configured to ignore input from the user 610 that falls within the deadband. The deadband element can be configured to only transmit inputs from the user 610 to the first summer 622 that are outside the deadband, e.g., that are above the predetermined minimum amount.

The first summer 622 of the computer system 602 can optionally not include the accumulator or the digital equivalent of an integrator. In this way, the user's input to the computer system 602 can represent a force directly instead of a force derivative that is integrated by the accumulator or integrator to a force command. The inclusion of the accumulator or integrator can allow for more delicate control of the surgical instrument by the user 610 since the first summer 622 can compensate for an inability of the user 610 to provide fine control, e.g., due to limitations of the master tool and/or limitations of human movement. The inclusion of the accumulator or integrator can allow the robotic surgical system 600 to provide a sustained force increment to the surgical instrument coupled to the movement mechanism 608, which can allow the user 610 to attend to other tasks during performance of a surgical procedure while the surgical instrument's output is adjusted. The omission of the accumulator or integrator can allow a brief force increment to be applied to the surgical instrument without the user 610 having to cancel the increment by applying the second input to the master tool that is in an opposite direction to the input that began the incremental force.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   first and second slave tools each having a working end configured to be positioned within a patient during performance of a surgical procedure;
   a master tool configured to be manually manipulated by a user to control the first and second slave tools; and
   a controller configured to be in electronic communication with the first and second slave tools and with the master tool, the controller being configured to receive a first input from the master tool indicating movement of the master tool and to cause the first slave tool to move in position in response to the received first input, and the controller being configured to receive a second input from the master tool indicating movement of the master tool and to adjust a force output of the second slave tool in response to the received second input, wherein the controller is configured to receive a third input from the master tool and, in response to receiving the third input, to cause subsequently received first inputs to control the second slave tool instead of the first slave tool and to cause subsequently received second inputs to control the first slave tool instead of the second slave tool.

2. The system of claim 1, wherein the first input indicates a change in position of the master tool, the controller being configured to cause the slave tool to move in position by either mimicking or mirroring the master tool's change in position indicated by the first input, and the second input indicates a change in position of the master tool, the controller being configured to translate an amount of the master tool's change in position indicated by the second input to an amount of the adjusted force output.

3. The system of claim 1, wherein the second input indicates a translational movement or a rotational movement of the master tool;

when the second input indicates the translational movement, adjusting the force output of the second slave tool in response to the received second input includes causing the second slave tool to rotate; and when the second input indicates the rotational movement, adjusting the force output of the second slave tool in response to the received second input includes causing the second slave tool to translate.

4. The system of claim 1, wherein the first and second tools are each configured to move in multiple degrees of freedom, and the first input indicates movement of the master tool in at least two of the multiple degrees of freedom, the controller being configured to cause the first slave tool to move in the at least two of the multiple degrees of freedom in response to the received first input, and the second input indicates movement of the master tool in one of the multiple degrees of freedom, the controller being configured to correlate the movement in the one degree of freedom to the force output.

5. The system of claim 1, further comprising a motor, the first input causing the controller to adjust a torque provided by the motor to the first slave tool, and the second input causing the controller to adjust a torque provided by the motor to the second slave tool.

6. A surgical method, comprising:

positioning a working end of a first slave tool relative to a first target relevant to performance of a surgical procedure on a patient;

positioning a working end of a second slave tool relative to a second target relevant to performance of the surgical procedure such that the second slave tool applies a force to the second target;

moving a master tool electrically coupled to the first and second slave tools, the movement of the master tool when the master tool is in a first mode of operation causing corresponding movement of the first slave tool relative to the first target, and the movement of the master tool when the master tool is in a second mode of operation causing an amount of the force applied to the second target to be changed by an amount corresponding to a scale of the movement of the master tool; and swapping modes of the master tool such that the movement of the master tool when the master tool is in the first mode of operation causing corresponding movement of the second slave tool relative to the second target, and the movement of the master tool when the master tool is in the second mode of operation causing an amount of a force applied to the first target by the first slave tool to be changed by an amount corresponding to the scale of the movement of the master tool.

7. A surgical method, comprising:

positioning a working end of a first slave tool relative to a first target relevant to performance of a surgical procedure on a patient;

positioning a working end of a second slave tool relative to a second target relevant to performance of the surgical procedure such that the second slave tool applies a force to the second target; and moving a master tool electrically coupled to the first and second slave tools, the movement of the master tool when the master tool is in a first mode of operation causing corresponding movement of the first slave tool relative to the first target, and the movement of the master tool when the master tool is in a second mode of operation causing an amount of the force applied to the second target to be changed by an amount corresponding to a scale of the movement of the master tool;

wherein the movement of the master tool is in multiple degrees of freedom, and the movement of the master tool when the master tool is in the first mode of operation causes the first slave tool to move in the multiple degrees of freedom relative to the first target, and the movement of the master tool when the master tool is in the second mode of operation does not cause the second slave tool to move in the multiple degrees of freedom relative to the second target.

8. A surgical method, comprising:

positioning a working end of a first slave tool relative to a first target relevant to performance of a surgical procedure on a patient;

positioning a working end of a second slave tool relative to a second target relevant to performance of the surgical procedure such that the second slave tool applies a force to the second target; and moving a master tool electrically coupled to the first and second slave tools, the movement of the master tool when the master tool is in a first mode of operation causing corresponding movement of the first slave tool relative to the first target, and the movement of the master tool when the master tool is in a second mode of operation causing an amount of the force applied to the second target to be changed by an amount corresponding to a scale of the movement of the master tool;

wherein the movement of the master tool when the master tool is in the second mode of operation includes movement of the master tool translationally or rotationally, and causing the amount of the force applied to the second target to be changed includes causing the second slave tool to move in the other one of translationally and rotationally.

* * * * *